United States Patent [19]

Mack et al.

[11] 4,201,289

[45] May 6, 1980

[54] PRIMARY PACKAGE FOR A SPACE AIR TREATING DEVICE

[75] Inventors: Frank J. Mack, Kinnelon; Walter M. Ronayne, Westfield, both of N.J.

[73] Assignee: American Home Products Corporation, New York, N.Y.

[21] Appl. No.: 935,193

[22] Filed: Aug. 21, 1978

[51] Int. Cl.² .............................................. B65D 85/70
[52] U.S. Cl. ...................................... 206/0.5; 249/117
[58] Field of Search ................ 206/0.5; 220/4 B, 4 E; 249/142, 117, 141; 425/DIG. 44, DIG. 57

[56] References Cited

U.S. PATENT DOCUMENTS

| | | | |
|---|---|---|---|
| 2,607,978 | 8/1952 | Ward | 249/55 |
| 2,798,631 | 7/1957 | Engel | 220/4 B |
| 2,809,863 | 10/1957 | Curran | 206/463 X |
| 3,103,428 | 9/1963 | Stello et al. | 249/142 X |
| 3,259,677 | 7/1966 | Zwick | 249/141 X |
| 4,078,761 | 3/1978 | Thompson | 425/435 X |

*Primary Examiner*—Stephen P. Garbe
*Attorney, Agent, or Firm*—Joseph Martin Weigman

[57] ABSTRACT

The disclosure is directed to a novel method of forming and packaging for display hollow, solid space air treating devices. A molten treating composition is charged into the outer shell of a thermoformed container which serves as a mold, as well as a display package for the finished product. An inner core is placed inside the outer shell displacing the molten material and forming a chamber of the shape and size of the device. A gas equalizing aperture permits release of internal pressure and excess molten material. The filled mold is cooled. The sealed container is suitable for shelf display but may have additional trade dress applied, if desired. The ultimate user removes the outer shell from the solidified device to activate the space air treatment feature.

4 Claims, 7 Drawing Figures

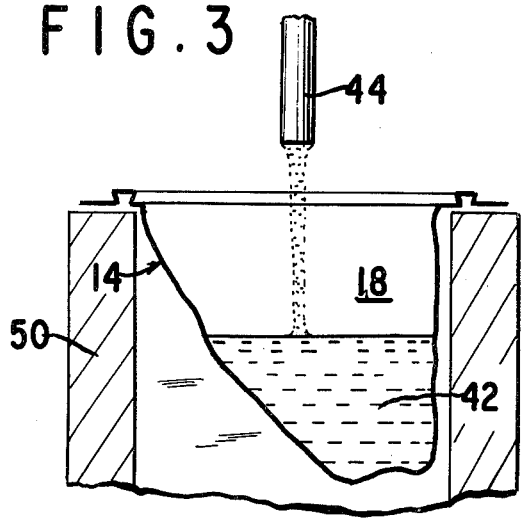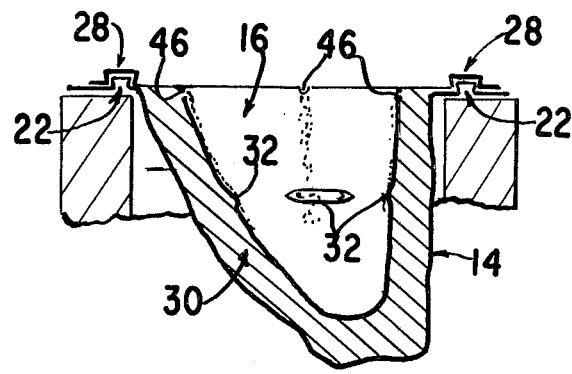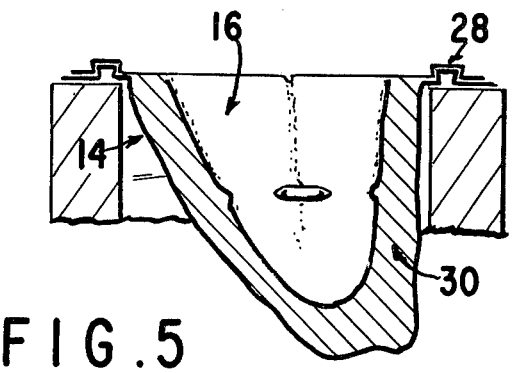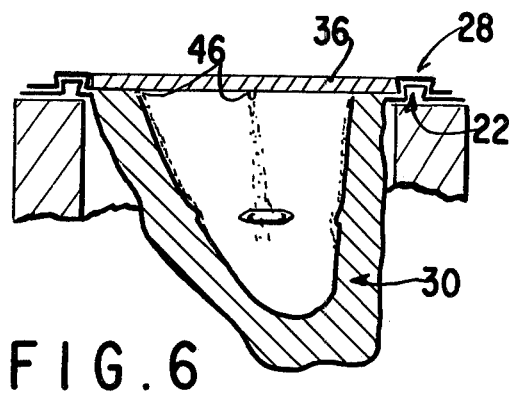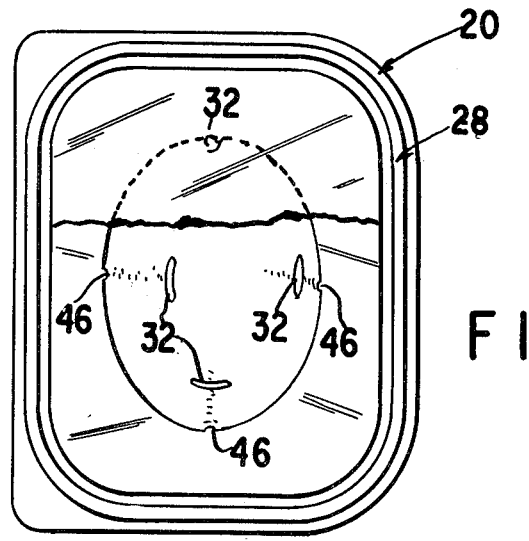

PRIMARY PACKAGE FOR A SPACE AIR TREATING DEVICE

This invention relates to space air treatment devices which have a solid, scented composition as the active ingredient. More particularly, it relates to solid, hollow room freshener devices and a method for forming them from a molten composition with great economy. Solid space air treating devices have been known which are formed by filling a molten composition through an orifice in the top of a container, closing the orifice and permitting the composition to solidify while in storage. Typically, such devices have a base, an upper closure sealably connected to the base and means to support the upper portion in spaced relation to the lower portion. When the user wants to activate the device, the upper portion is moved away from the base a predetermined distance, and room air through natural convection crosses its surface and is freshened by the active ingredients. Such devices are extremely popular, but the containers are expensive and account for a disproportionate portion of the selling price of the treating device. The devices are typically made of carrageenan which shrinks as it becomes dehydrated and presents an unattractive appearance at the later stages of its effectiveness.

Other devices are known in which a molten active ingredient is charged into a container having a decorative arrangement of openings on its surface. The openings are then closed with a pressure sensitive material. The user activates the devices by removing the pressure sensitive material. The devices are cheaper than those described above. Their attractiveness depends on the ornamental appearance of the container in which they were packaged.

The most closely related prior art is our co-pending application Ser. No. 770,343 filed Feb. 22, 1977 now abandoned for a primary package for a space air treating device and method of forming said device. In that application is disclosed a method and the resultant product of producing a hollow, solid, space air treating device by rotational molting. The advantage of the present invention is that the need for expensive rotational molding equipment is obviated.

It is an object of the present invention to provide a space air treating device in which the active ingredient is made in an ornamental appearance.

It is another object of the present invention to provide a space air treating device which is hollow and, being made of nonshrinkable composition, does not tend to shrink or deteriorate in appearance during use.

It is still another object of the present invention to provide an economical method for manufacturing space air treating devices which are ornamental in appearance.

Other and further objects of the invention will be apparent to those skilled in the art from reading the following description in conjunction with the drawings in which.

Figure 2:
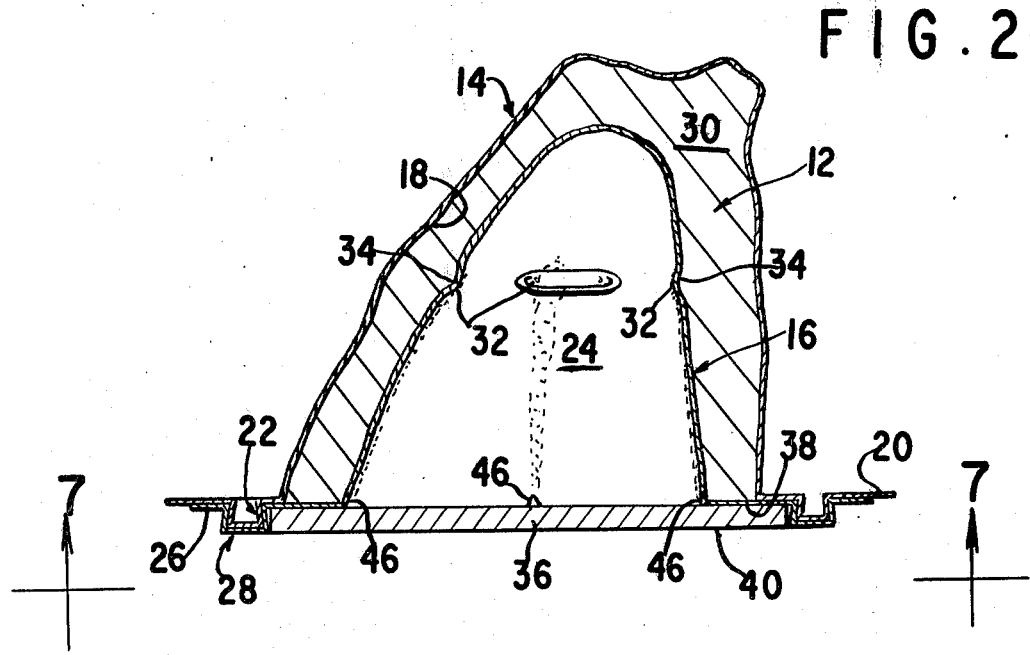
FIG. 2 is a cross-sectional view of the device taken generally along lines 2—2 of FIG. 1.

FIGS. 3, 4, 5 and 6 show successive steps in the manufacture of the device, FIG. 3 showing the outer shell being inverted and filled with molten material, FIG. 4 showing the inner core inserted into the molten material with excess material being vented, FIG. 5 showing the solidified device, and FIG. 6 showing the label in place in the finished device; and FIG. 7 is a bottom view of the device of FIG. 2.

The objects of the invention may be achieved with a combination mold and primary package made up of an outer shell, an inner core and a solid, hollow, space air treating device disposed between the outer shell and inner core. The outer shell is further comprised of a cavity formed in its center and having a predetermined pattern which is a replica of the external shape of the final product and has a flange surrounding the cavity with sealing means defined in the flange which entirely surround the cavity. The inner core, which is designed to extend into the outer shell, has a cavity formed in its center which is smaller than the outer shell cavity and with the outer shell cavity defines a chamber to contain the solid, air treating device. The inner core further has a flange surrounding the cavity and sealing means in the flange cooperating with the sealing means on the outer shell to form a liquid tight seal. The solid, hollow, space air treating device is formed in place in the chamber between the inner core and the outer shell and, after cooling and solidification, the air treating device may be stored in the same sealed package formed by the outer shell and inner core. The activation of the device for air treating may be accomplished by removal of the outer shell.

Figure 1:
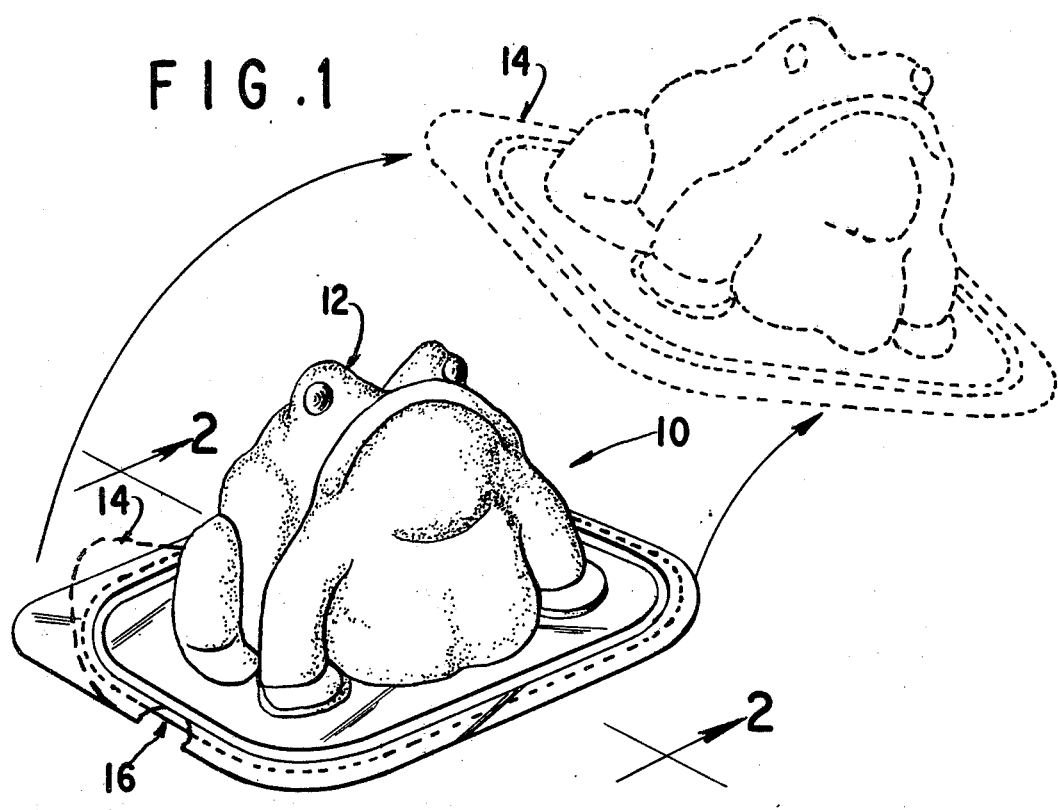
FIG. 1 is a perspective view of a hollow, ornamental space air treating device at the time of removal of the outer shell.

The combination 10 of an air treating device, or pomander 12, and a mold-package is shown in FIG. 1. The mold-package is further made up of an outer shell 14 and an inner core 16. As is shown in FIG. 1, the outer shell 14 (shown in phantom) may be removed at the point of use to expose the pomander 12 and activate its use as a space air treating device.

The outer shell 14 is formed, for instance by thermoforming, from a planar sheet of material, such as plastic, and has a cavity 18 formed in its center in a predetermined pattern which is a replica of the external surface of the final product. A flange 20 surrounds the cavity. A sealing means 22, such as the tongue of a tongue and groove joint, is defined in the flange and extends entirely around the cavity.

The inner core 16 is formed, for instance by thermoforming, from a thin sheet of plastic and has a cavity 24 formed in its center. A flange 26 surrounds the cavity and has formed in it a sealing means 28, such as the groove of a tongue and groove joint, which completely surrounds the cavity and is adapted to cooperate with the sealing means of the outer shell to form a liquid tight seal. The cavity 24 of the inner core 16 extends into the cavity 18 of the outer shell 14 and displaces the molten material and defines a chamber 30. The chamber 30 contains the molten material, as will be further described below, and, after solidification of the molten material, contains the solid, hollow, pomander 12 which completely fills the chamber 30.

The pomander 12 may take any shape that is found desirable, such as the frog which is shown in the drawings. A principal limitation on the shape of the pomander is that it may contain no undercuts on its outer surface which would interfere with removal of the outer shell. That is, the pomander must be largest at its bottom or point near the flange 20 and taper continuously, albeit irregularly, to the inner-most extension of the cavity 18.

Contrariwise, while the cavity 24 of the inner core generally follows the shape of the cavity of the outer shell, it has been found desirable that the inner core contain undercuts 32. The undercuts result in the formation of protrusions 34 in the inner surface of the pomander 12. The protrusions and undercuts combine to retain the solid pomander in engagement with the inner core. Thus, when the outer shell is removed, the pomander 12 remains fastened to the inner core which may serve as a base for display. The presence of a base is important because preferred formulations for the pomander composition contain essential oils which may undesirably mark the surface of fine furniture, if placed in contact with it.

It has also been found advantageous to apply an indicia receptor 36 to the inner core on the side opposite the pomander 12. In one form, the indicia receptor 36 may be a stiff cardboard which may be snap fitted inside the sealing means 28. On its upper surface 38 the indicia receptor may have printed a design which coordinates with the figure represented in the pomander. For instance, where the pomander is a frog, the upper surface 38 may be printed to represent grass or lily pads. The material of the inner core is preferably transparent although it may be pigmented to enhance the appearance of the combination. Similarly, the lower surface 40 of the indicia receptor 36 may be used as a label for a trademark, manufacturer's identification, and any other label information desired.

As an alternate, the indicia receptor may be designed to fit within the lower surface of the cavity. As another alternative, the flange 26 of the inner core may be embossed to represent grass or lily pads in coordination with the figure represented by the pomander.

The method of using the outer shell and inner core for displacement molding of a molten material to form a pomander is best seen in FIGS. 3, 4, 5 and 6. In FIG. 3, an outer shell 14 is inverted with cavity 18 downward. A molten composition 42 is dispensed into the outer shell while it is supported by a puck, or assembly fixture 50. The amount of the molten composition is predetermined and may be dispensed by a filler 44, such as a premeasured piston filler. The inner core 16 is then placed inside the outer shell 18 and displaces the molten material 42 as it is moved into position and sealably engages the outer shell by the engagement of the sealing means 22 and 28. Desirably, the molten material exactly fills the chamber 30. However, it is preferred that one or more apertures 46 be provided in the inner core adjacent to the flange. The apertures 46 serve to vent any gas which may be trapped in the molten material or within the chamber when the inner core and outer shell are sealed together. Also, the apertures 46 permit any slight excess of molten material to float out of the inner core on to its inner surface and solidify there. This assures that there will be no undesirable "flash" formed around the base of the pomander which would be visible from the outside. The amount of the molten material charged into the outer shell is controlled so that the excess material is minimal.

It is to be understood that various modifications of the foregoing may be made. For instance, the outer shell 18 may be assembled from two or more sections. Such multi-section shells permit latitude in the shape of the pomander by eliminating the necessity to avoid undercuts, inter alia.

What is claimed is:
1. A combination mold and primary package for a space air treating device comprising:
  A. an outer shell having
    1. a cavity formed in its center in a predetermined pattern which is a replica of the shape of the space air treating device;
    2. a flange surrounding said cavity;
    3. sealing means defined in said flange entirely around said cavity;
  B. an inner core extending into said outer shell and having
    1. a cavity formed in its center, said cavity being smaller than said outer shell cavity, and with said outer shell defining a chamber;
    2. a plurality of undercuts defined on the chamber side of said cavity;
    3. a flange surrounding said cavity;
    4. sealing means defined in said flange entirely surrounding said cavity and cooperating with said outer shell sealing means to form a liquid tight seal; and
  C. a hollow, space air treating device formed of a solid material disposed in said chamber and filling said predetermined pattern whereby said air treating device may be stored with said outer shell and inner core sealed together and may be activated by the removal of said outer shell.

2. A combination mold and primary package for a space air treating device comprising:
  A. an outer shell having
    1. a cavity formed in its center in a predetermined pattern which is a replica of the shape of the space air treating device;
    2. a flange surrounding said cavity;
    3. sealing means defined in said flange entirely around said cavity;
  B. an inner core extending into said outer shell and having
    1. a cavity formed in its center, said cavity being smaller than said outer shell cavity, and with said outer shell defining a chamber;
    2. a flange surrounding said cavity;
    3. sealing means defined in said flange entirely surrounding said cavity and cooperating with said outer shell sealing means to form a liquid tight seal;
    4. an indicia receptor connected to said inner core flange on the side opposite said outer shell flange; and
  C. a hollow, space air treating device formed of a solid material disposed in said chamber and filling said predetermined pattern whereby said air treating device may be stored with said outer shell and inner core sealed together and may be activated by the removal of the said outer shell.

3. A combination mold and primary package for a space air treating device as defined in claim 1 or 2 further comprising at least one aperture defined in said inner core adjacent said flange.

4. A combination mold and primary package for a space air treating device as defined in claim 1 or 2 wherein said space air treating device is in the form of a frog.

* * * * *